United States Patent
Pourmanafzadeh (10) Patent No.: US 6,931,746 B2
(45) Date of Patent: Aug. 23, 2005

(54) METHOD AND APPARATUS FOR LEG LENGTH DISCREPANCY MEASUREMENT

(76) Inventor: Unes Pourmanafzadeh, 5701 Barker Ridge Dr., Austin, TX (US) 78759

( * ) Notice: Subject to any disclaimer, the term of this patent is extended or adjusted under 35 U.S.C. 154(b) by 0 days.

(21) Appl. No.: 10/320,846

(22) Filed: Dec. 16, 2002

(65) Prior Publication Data

US 2004/0111909 A1 Jun. 17, 2004

(51) Int. Cl.$^7$ ............................. A41H 1/02; G01B 3/02
(52) U.S. Cl. ......................................... 33/512; 33/1 BB
(58) Field of Search ..................... 33/512, 515, 1 BB, 33/1 B (56) References Cited

U.S. PATENT DOCUMENTS

| | | | | |
|---|---|---|---|---|
| 2,111,648 A | * | 3/1938 | Stone | 33/512 |
| 2,619,729 A | * | 12/1952 | De Jarnette | 33/515 |
| 2,780,004 A | * | 2/1957 | Rosenbaum | 33/512 |
| 3,196,551 A | | 7/1965 | Prouost | |
| 4,539,754 A | | 9/1985 | Antony | |
| 4,635,367 A | * | 1/1987 | Vigede | 33/512 |
| 4,823,476 A | * | 4/1989 | Curtin | 33/512 |
| 4,883,066 A | | 11/1989 | Widdoes | |
| 5,060,393 A | | 10/1991 | Silverman | |
| 5,088,504 A | | 2/1992 | Benesh | |
| 5,435,321 A | | 7/1995 | McMillen | |
| 5,490,518 A | | 2/1996 | Russo | |
| 5,700,268 A | | 12/1997 | Bertin | |
| 6,027,507 A | | 2/2000 | Anderson | |
| 6,073,359 A | | 6/2000 | Lee | |
| 6,128,824 A | | 10/2000 | Yang | |
| 6,193,724 B1 | | 2/2001 | Chan | |
| 6,383,149 B1 | | 5/2002 | DeMayo | |

FOREIGN PATENT DOCUMENTS

WO    WO 01/39654 A2    6/2002

* cited by examiner

Primary Examiner—Christopher W. Fulton
(74) Attorney, Agent, or Firm—Rick B. Yeager (57) ABSTRACT

An apparatus and method for determining difference in leg height of a standing patient by making a first measurement while the patient stands on a first foot, making a second measurement while the patient stands on a second foot, and determining the vertical distance between the first measurement and the second measurement. One embodiment incorporates a scale with a sliding wide measurement plate to measure the top of the head. Another embodiment provides a wide height measurement plate to retrofit existing height scales, and a fabrication kit for making that plate. In another embodiment the patient wears an apron with reference markings which may be observed through a movable reference grid. The observation may be manual or optically with a camera or scanner.

4 Claims, 11 Drawing Sheets

METHOD AND APPARATUS FOR LEG LENGTH DISCREPANCY MEASUREMENT

FIELD OF THE INVENTION

The present invention relates to a method and apparatus for measuring the difference in leg length for a patient.

BACKGROUND OF THE INVENTION

Doctors and other medical personnel are often interested in obtaining data with respect to the physical measurements of the legs of a patient. When one leg is larger than the other, a person does not distribute forces of weight uniform to his or her feet or knees, and this unequal weight distribution may cause knee ache, backache etc. In some cases, it is desirable to determine if leg length is equal before conducting chiropractic treatment.

The differences in leg length may be aggravated or may develop with age as the stronger leg grows more than a weaker leg.

Untreated differences in leg length can cause pain such as in the knee, back, or neck. On the other hand, if the differences in leg length are known, then the differences can be compensated, such as by shoe sole inserts.

It is desirable to a device and method for provide simple and reliable leg length difference measurements so that problems can be identified early and treated.

The prior art includes a variety of techniques for measuring skeletal dimensions including leg length or lower leg length for applications such as monitoring growth of children, chiropractic skeletal analysis, and hip replacement. Most of the prior art patents require measurement in a lying or sitting position.

U.S. Pat. No. 5,776,082 describes an apparatus for taking range of motion measurements including leg length by referencing the suprasternal notch.

U.S. Pat. No. 5,088,504 describes an apparatus which records the weight transmitted by each foot while a patient is standing on the device.

SUMMARY OF THE INVENTION

The current invention provides relatively simple methods for determining leg length of a standing patient. In one embodiment, a height scale is used to obtain a first measurement using a reference point such as the top of the patient's head while the patient stands on one foot. This first measurement is related to the length of the patient's first leg. A second measurement is obtained while the patient stands on his or her other foot. This second measurement is related to the length of the patient's second leg, and the difference between the first and second measurement is the difference in length of the first leg and the second leg. In this embodiment, the measurement is preferably taken with a wide plate so that a measurement can be taken when the patient's head tilts slightly due to standing on one foot or the other. The patient may stand directly on the floor and alternate weight between his or her feet.

In another embodiment, the patient wears an apron with reference markings, and a first measurement is taken relative to a grid fixed at a convenient location while the patient stands on a first foot. A second measurement is taken relative to the fixed grid while the patient stands on a second foot. The measurements may be taken manually, such as through a transparent sheet with a reference grid; or may be taken with an electronic observation and recording device such as a scanner or a camera. The observation and recording device typically views the reference markings through a reference grid which is set at a convenient height. In this embodiment, a movable frame typically holds the reference grid and the observation and recording device. The observation height is typically established by moving the frame on guide rails to a desired height and clamping the device in place.

The invention provides an accurate, simple, and inexpensive method for measuring the difference of two legs under load of the weight of body.

DETAILED DESCRIPTION OF EMBODIMENT—MEASUREMENT PLATE FOR VERTICAL SCALE

Figure 1A:
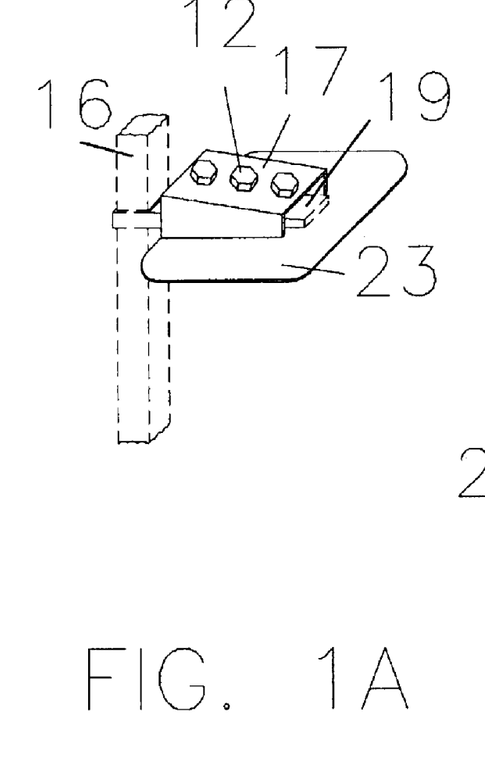
FIG. 1A is a top perspective view of a measurement plate and mounting bracket for retrofit of an existing height scale.

Referring to FIG. 1A, which is a top perspective view of a measurement plate 23 and mounting bracket 17 for retrofit of an existing height scale 16, the mounting plate bracket 17 is affixed to the height measurement arm 19 of the scale. The patient stands on a first foot and a first height reading is taken relative to a reference point on the patient. In this embodiment, the reference point is the highest point on the patient's head, and the point is determined by moving the measurement plate 23 to rest on the patient's head. The patient then stands on his or her second foot and a second height reading is taken relative to the reference point. The difference in leg height is determined by subtracting the first reading from the second reading. The actual height measurement does not necessarily correspond to an actual body dimension of the patient, it is the difference in readings that is sought.

Figure 1B:
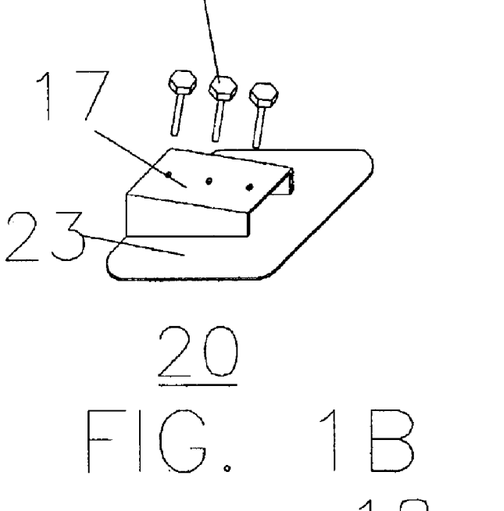
FIG. 1B is an exploded view of the measurement plate and mounting bracket of FIG. 1A.

Referring now to FIG. 1B, which is an exploded view of the measurement plate and mounting bracket of FIG. 1A, the measurement plate 23 and mounting bracket 17 may be secured to an arm of the height measuring devise by screws 12. In this embodiment the measurement plate 23 is at least 200 mm by 200 mm; and is preferably 300 mm by 300 mm, so that as a patient stands on one foot, the measurement plate can be positioned at the highest point on the patients head, even if the head is tilted off-center. When a patient stands on one foot, the patient tends to stand at a slight tilt.

Figure 1C:
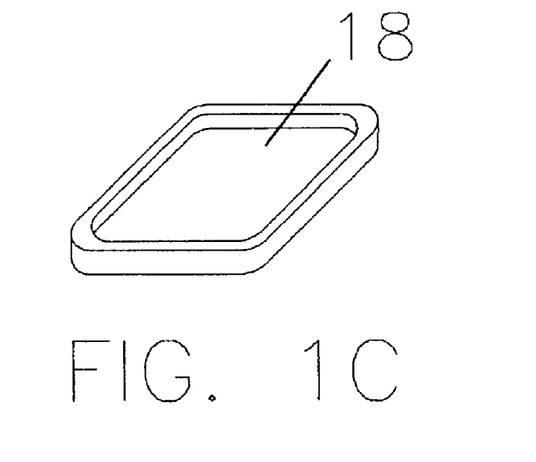
FIG. 1C is a top perspective view of a molding frame for the measurement plate and mounting bracket of FIG. 1A.

Referring now to FIG. 1C, which is a top perspective view of a molding frame for the measurement plate and mounting bracket of FIG. 1A, the measurement plate may be formed from a plastic material such as polyurethane or epoxy. For instance, the plate may be formed by pouring a polyurethane material into a mold 18 and permitting the polyurethane to cure. In one embodiment, the measurement plate may be provided as a kit of a plastic and a mold so that a customer can make the measurement plate. In one embodiment, the kit may permit casting a measurement plate around the measurement arm of an existing height measurement device. In other embodiments, the measurement plate may be an injection molded plastic or a metal.

Detailed Description of Embodiment—Height Scale with Measurement Plate

Figure 2A:
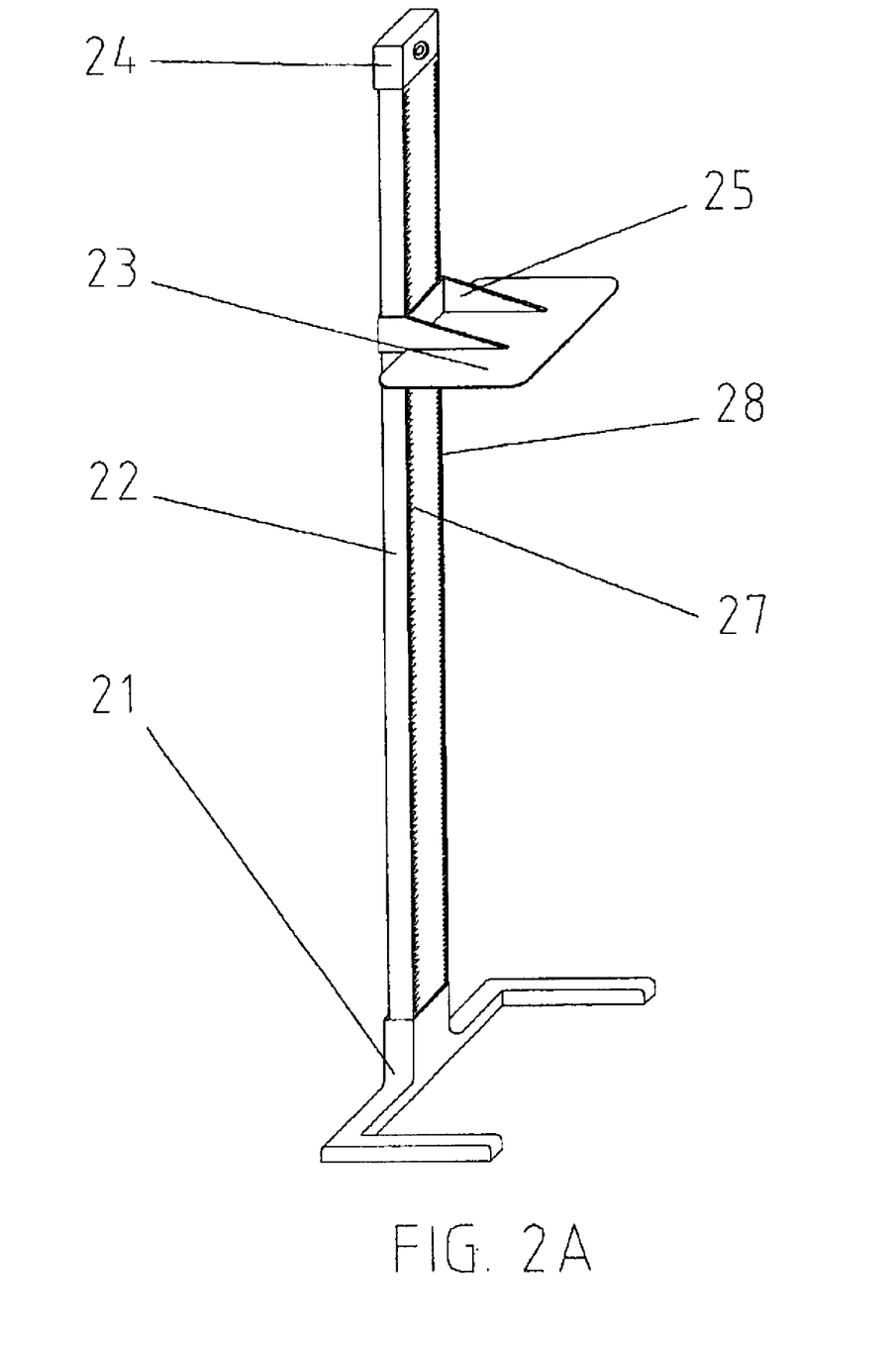
FIG. 2A is a perspective view of a height measuring device.

Referring to FIG. 2A, which is a perspective view of a vertical scale for use with the foot support, measurements are obtained from ruled scale on the front face of the vertical scale 22. In the embodiment shown, rulings are provided on both sides of the front face, preferably so that one set of rulings 28 is in metric units and the other set 27 is in English units. The vertical scale is supported vertically by a floor support stand 21, which in this case is two support legs spaced apart sufficiently for the support block and a patient to be positioned between the legs. The vertical scale may also be attached to a wall, such as by the mounting hole 24 shown at the top of the scale. In the wall mounting embodiment, the vertical scale is mounted so that the ruled scale is held vertically. In this case, the height determination means is a measurement plate 23 such as described above. The measurement plate is movably attached to the vertical scale with a mounting bracket 25 so that the plate may be slid up or down the scale. The scale mounting bracket 25 engages the plate mounting bracket 17 and holds the plate perpendicular to the vertical scale so that each point on the bottom of the plate is at the same height from the floor.

Detailed Description of Embodiment—Vertical Scale and Measurement Plate Method In this embodiment, the patient stands in front of a vertical scale with his or her weight on a first foot to obtain a first measurement, and then stands with his or her weight on a second foot to obtain a second measurement.

Figure 2B:
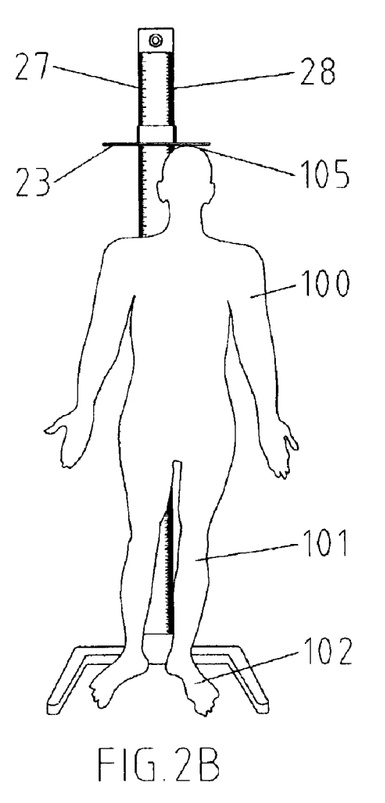
FIG. 2B is a front perspective view of a patient standing on a first foot in front of the height measuring device of FIG. 2A.

Referring now to FIG. 2B, which is a perspective view of a patient 100 standing next to the vertical scale, the patient stands on a first foot 102 on the floor so that his or her weight is on the first leg 101. The measurement plate 23 has been moved to rest on the highest portion of the patient's head 105.

Figure 2C:
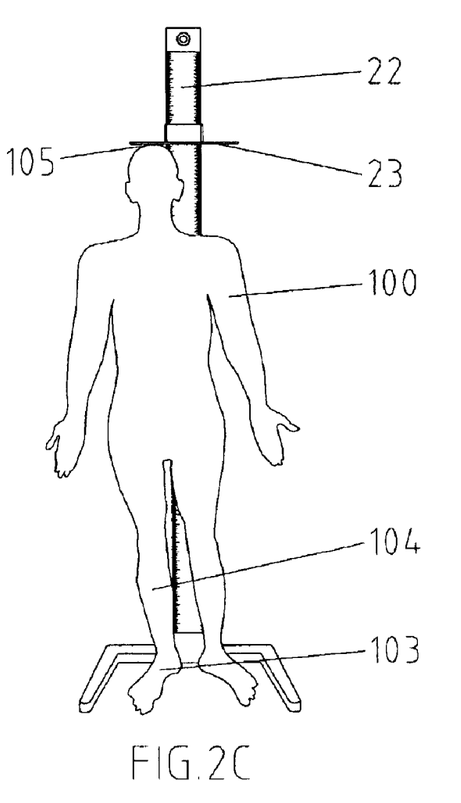
FIG. 2C is a front perspective view of a patient standing on a second foot in front of the height measuring device of FIG. 2A.

Referring now to FIG. 2C, which is a perspective view of a patient 100 standing next to the vertical scale 22, the patient stands on a second foot 103 on the floor so that his or her weight is on the second leg 104. The measurement plate 23 has been moved to rest on the highest portion of the patient's head 105.

The plate preferably is moved to rest on the highest point on a patient's head so that a first height measurement may be recorded as the patient stands on a first foot. The adjustable measurement plate is then moved upwards so that the patient can stand on his or her second foot. The plate is slid down the vertical scale 22 until the plate reaches the highest point on the patient's head 105 and a second measurement is recorded. The difference in leg height is obtained by subtracting the first and second measurements. For instance if the first height reading is 71.00 inches, and the second height reading is 70.80 inches, then the first leg 101 is determined to be 0.20 inches longer than the second leg 104. A negative result indicates that the first leg is shorter than the second leg.

Figure 3A:
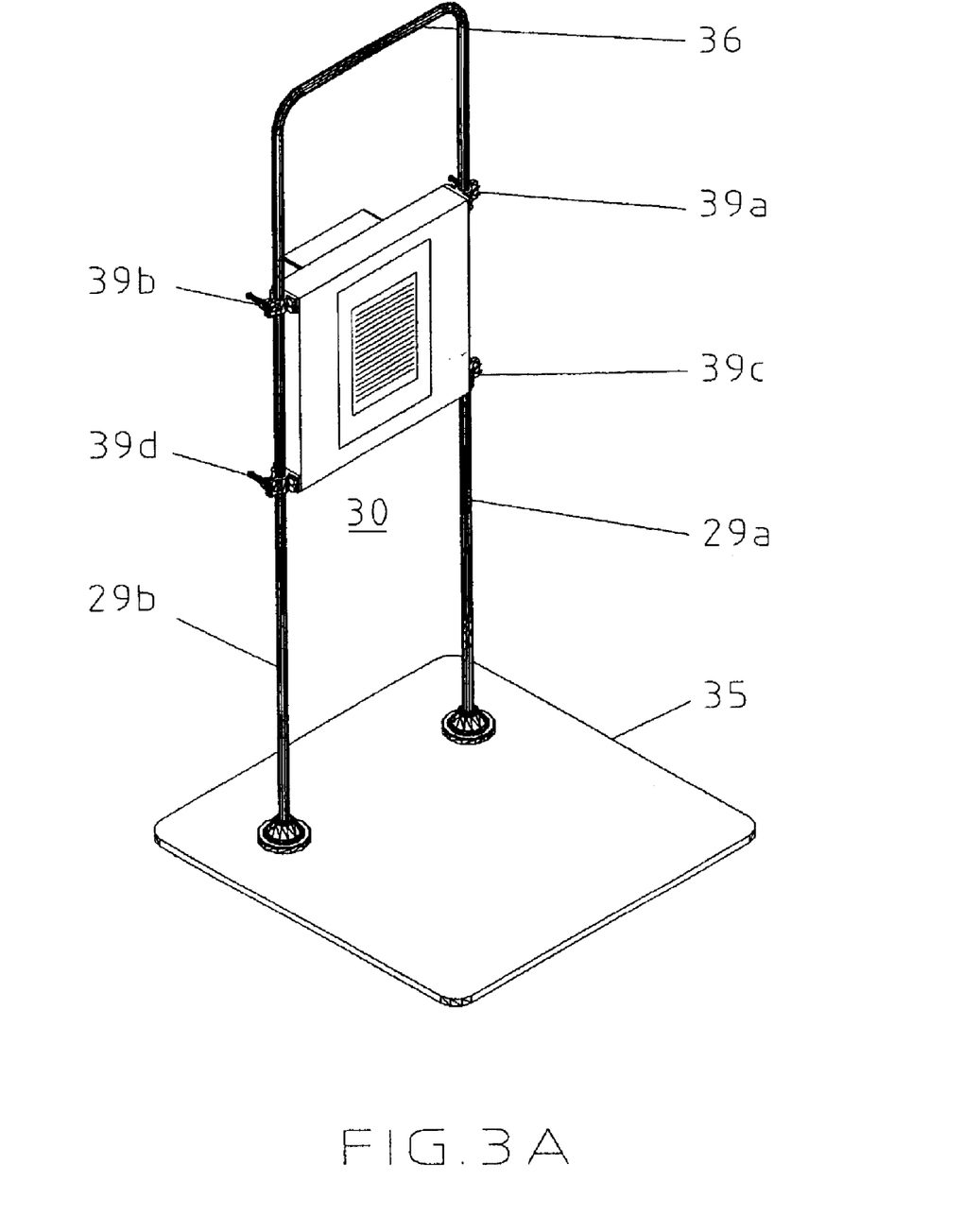
FIG. 3A. is a perspective view of a height observation and recording device.
Figure 3B:
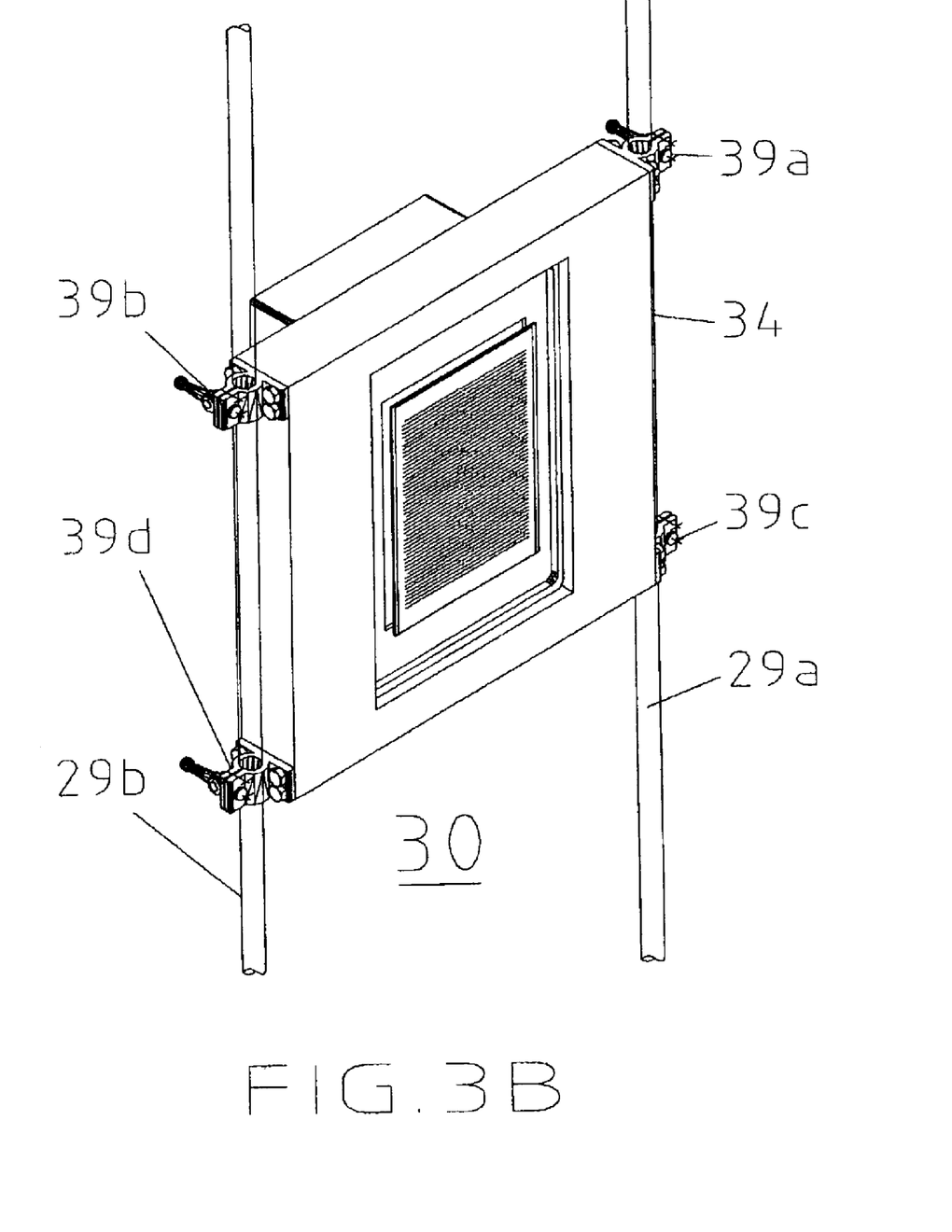
FIG. 3B. is an enlarged front perspective view of a height observation and recording device.
Figure 4:
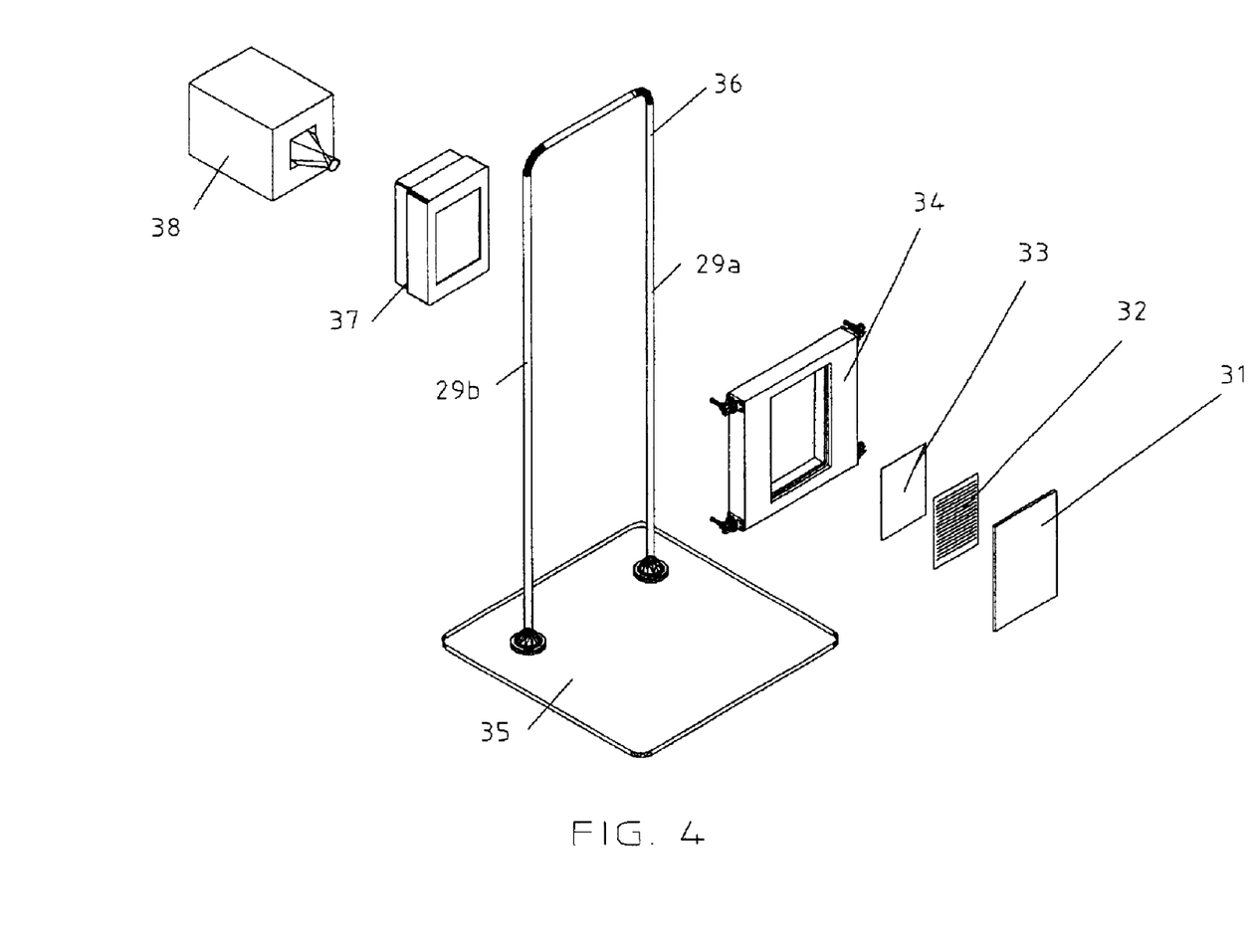
FIG. 4. is an exploded view of the height observation and recording device of FIG. 3.

Detailed Description of Embodiment—Reference Point Observation and Recording Referring now to FIG. 3A, FIG. 3B, and FIG. 4 which are front views and an exploded view of a reference point observation and recording embodiment, an observation and recording device assembly 30 is movably mounted on a frame 36 supported by a floor support 35. Alternatively, the observation and recording device may be wall mounted. In this embodiment, the frame is comprised of a first side rail 29a and a second side rail 29b. Brackets 39a–39d hold the device on the rails so that the device can be slid up and down the rails. When the device is located at a desired height, one or more bracket clamp is set to hold the device at the desired position. The observation and recording device can be electro-optical such as a scanner 37, camera or digital camera 38, or copier. In alternate embodiments, the observation and recording device can be a technician making a manual reading. The reference grid 32 may be held in place by a frame 34 and glass cover sheets 31 and 33.

Figure 5:
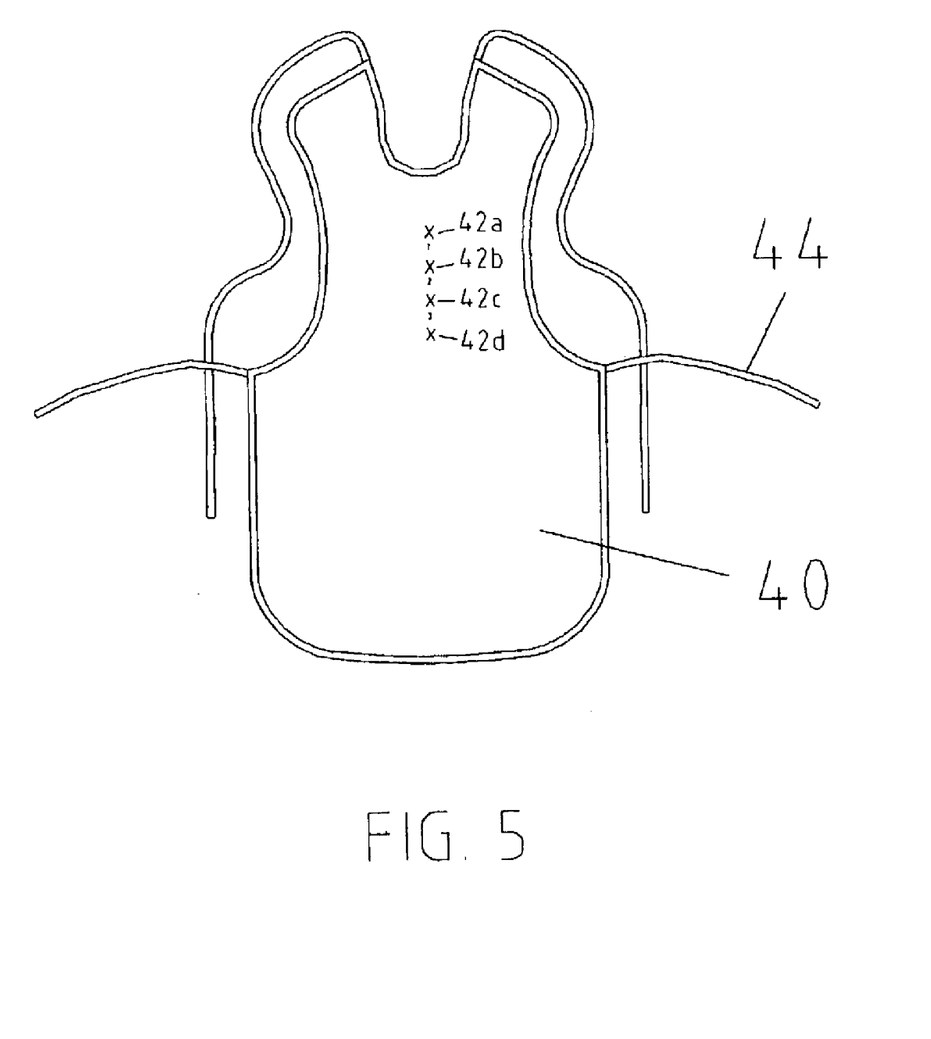
FIG. 5 is a front view of an apron with reference markings.

In this embodiment, the patient will put on special marked apron and stand on one foot in front of a window of scanning device. Referring now to FIG. 5, which is a front view of an apron 40, the apron may be worn by a patient during the height measurement. The apron may include a plurality of reference markings, illustrated by points 42a–42d. These reference markings establish one or more reference points for taking height measurements in order to determine differences in leg length. The apron may be tied onto the patient with tie strings 44. In alternative embodiments, reference mark may be provided on other articles such as shirts or gowns, or the marks may be placed directly in the patient such as by a removable sticker.

Figure 6:
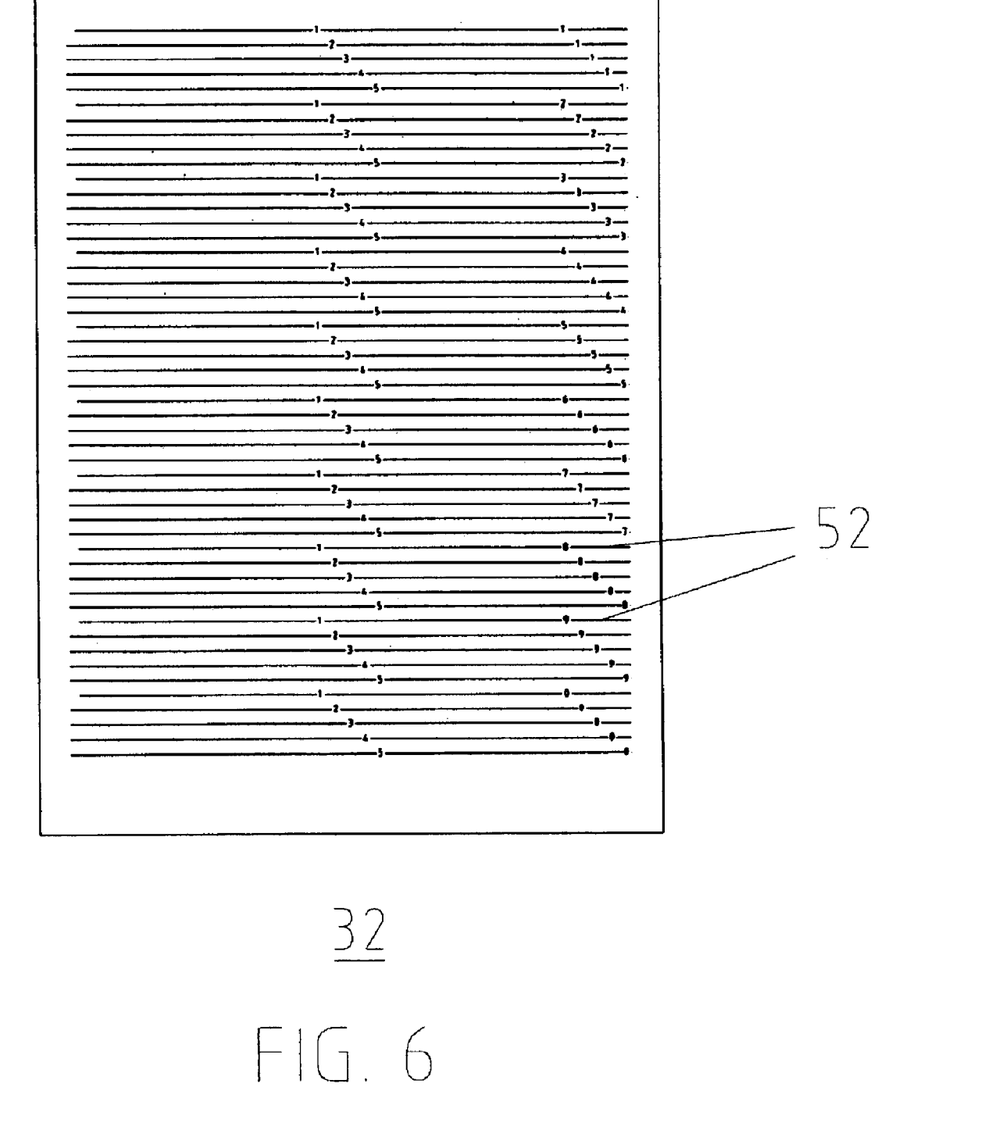
FIG. 6 is a front view of a reference grid for the height observation and recording device of FIG. 3A.

Referring now to FIG. 6, which is detailed view of a reference grid 32, the grid may include reference lines 52 which can be used to determine the height of a reference mark on the apron. The grid is preferably provided on a transparent sheet so that reference marks may be observed through the grid.

Figure 7A:
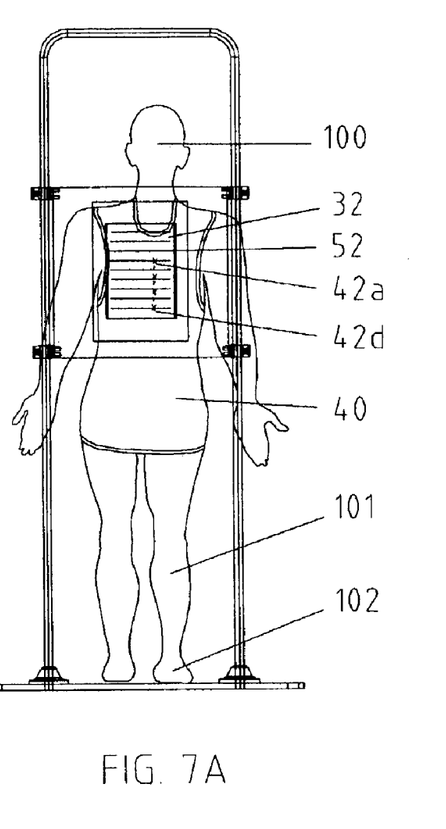
FIG. 7A is a front view of a patient standing on a first foot in front of the height observation and recording device of FIG. 3A.
Figure 8A:
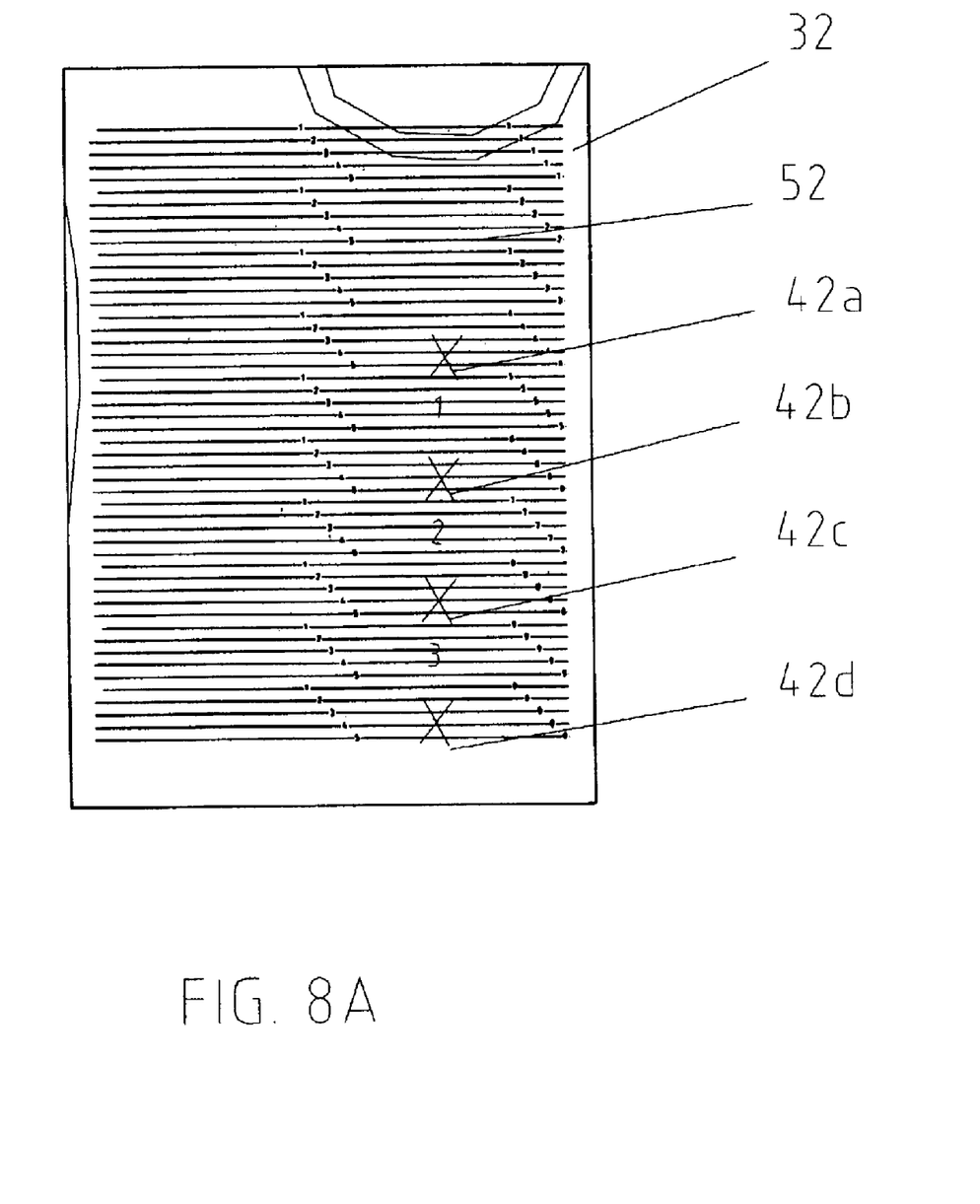
FIG. 8A is a front view of reference markings visible through the reference grid for the measurement of FIG. 7A.

Referring now to FIG. 7A, which is detailed view of a patient 100 stranding on a first foot 102 in front of the reference point observation and recording embodiment, the reference points 42a–42d are observable through the reference grid 32 and may be recorded with respect to one or more reference grid lines 52. Referring now to FIG. 8A, the position of the reference points 42a–42d with respect to the reference grid 32 and reference grid lines 52a may be observed and recorded.

Figure 7B:
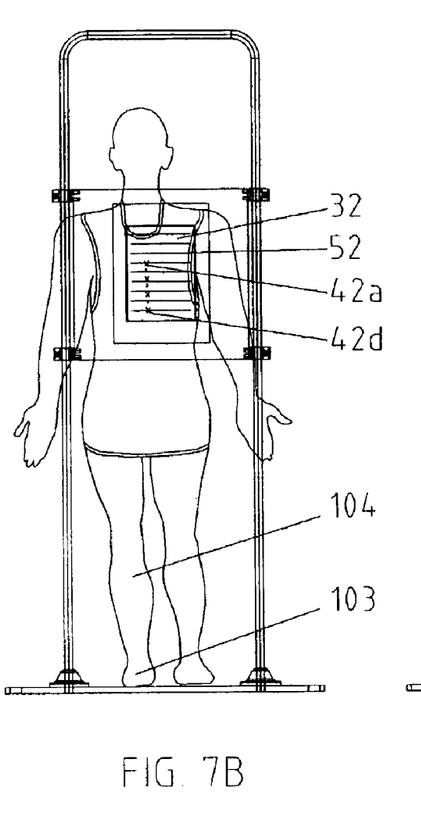
FIG. 7B is a front view of a patient standing on a second foot in front of the height observation and recording device of FIG. 3A.
Figure 8B:
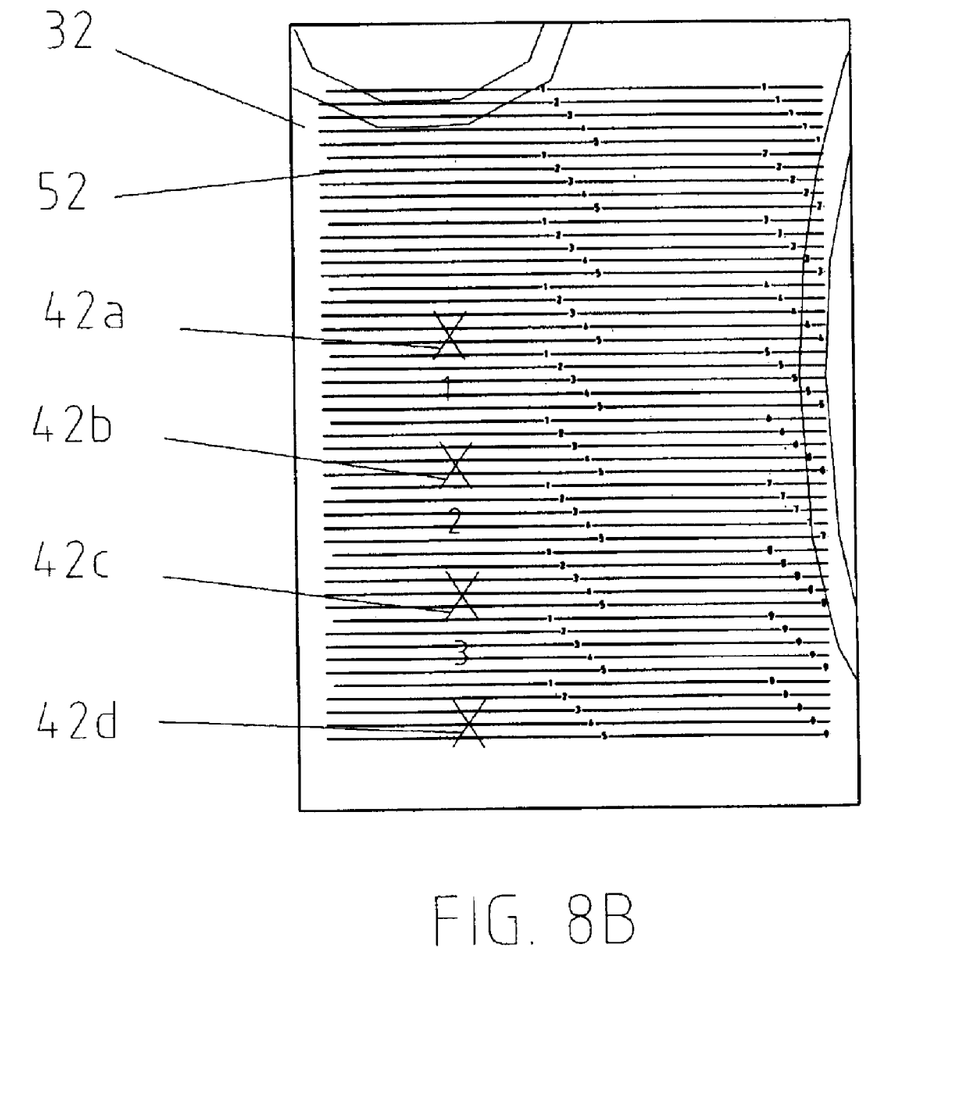
FIG. 8B is a front view of reference markings visible through the reference grid for the measurement of FIG. 7B.

Referring now to FIG. 7B, which is detailed view of a patient 100 standing on a second foot 103 in front of the reference point observation and recording device, the reference points 42a–42d are observable through the reference grid and may be recorded with respect to one or more reference grid lines 52b. Referring now to FIG. 8b, the position of the reference points 42a–42d with respect to the reference grid 32 and reference grid lines 52b may be observed and recorded. In this embodiment, the grid lines are preferably spaced 5 mm apart.

The distance between these observed reference points is a measurement of the difference in leg heights.

In some embodiments, the image may be printed or stored on a computer for future reference.

Detailed Description of Embodiment—Fixed Reference Grid Observation and Recording In this embodiment, a device similar to that described above is employed, except that the reference grid is mounted in a fixed location. In this embodiment, the reference grid is tall enough to provide measurement of both tall and short patients without moving the grid.

What is claimed is:

1. A method for measuring differences in leg length of a patient, the method comprising:
    positioning the standing patient adjacent to a vertical scale, the scale having a measurement plate, while the patient stands on a first foot;
    sliding the measuring plate to the top of the patient's head;
    obtaining a first measurement by reading a height of a portion of the measurement plate relative to the vertical scale;
    sliding the measurement plate away from the patient's head;
    positioning the standing patient adjacent to the vertical scale, while the patient stands on a second foot;
    obtaining a second measurement by reading the height of a portion measurement plate relative to the vertical scale; and
    attributing the difference between the first measurement and the second measurement to the difference in leg length.

2. A method for measuring differences in leg length of a patient, the method comprising:
    providing at least one externally visible reference point for the patient;
    providing a substantially transparent reference grid, such that the reference point may be viewed through the reference grid, and such that the vertical position of the reference point may be observed and recorded relative to the grid;
    instructing the patient to stand in proximity to the reference grid while placing substantially all of the patient's weight on a first foot;
    making a first measurement by recording the position of the reference point relative to the reference grid;
    instructing the patient to stand in proximity to the reference grid while placing substantially all of the patient's weight on a second foot;
    making a second measurement by recording the position of the reference point relative to the reference grid;
    determining the vertical distance differences between the first measurement the second measurement; and
    attributing the vertical distance difference to the difference in leg height.

3. The method of claim 2 wherein providing at least one externally visible reference point for a patient comprises:
    the patient wearing an apron having at least one reference mark.

4. A method for measuring differences in leg length of a patient, the method comprising:
    instructing the patient to stand while placing substantially all of the patient's weight on a first foot;
    determining a first vertical position of a reference point relative to the patient;
    instructing the patient to stand while placing substantially all of the patient's weight on a second foot;
    determining the second vertical position of the reference point relative to the patient;
    determining the vertical distance difference between the first vertical position of the reference point and the second vertical position of the reference point; and
    attributing the vertical distance difference to the difference in leg height.

* * * * *